US 9,475,757 B2

(12) United States Patent
Muthukrishnan et al.

(10) Patent No.: US 9,475,757 B2
(45) Date of Patent: Oct. 25, 2016

(54) SYNTHESIS OF ANTI-PARKINSON AGENT (71) Applicant: Council of Scientific & Industrial Research, New Delhi (IN)

(72) Inventors: Murugan Muthukrishnan, Pune (IN); Mohammad Mujahid, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/888,697

(22) PCT Filed: May 2, 2014

(86) PCT No.: PCT/IN2014/000294
§ 371 (c)(1),
(2) Date: Nov. 2, 2015

(87) PCT Pub. No.: WO2014/178083
PCT Pub. Date: Nov. 6, 2014

(65) Prior Publication Data
US 2016/0060211 A1    Mar. 3, 2016

(30) Foreign Application Priority Data

May 3, 2013   (IN) .......................... 1307/DEL/2013

(51) Int. Cl.
| | |
|---|---|
| *C07C 231/12* | (2006.01) |
| *C07C 237/06* | (2006.01) |
| *C07C 41/01* | (2006.01) |
| *C07C 41/18* | (2006.01) |
| *C07C 303/40* | (2006.01) |
| *C07C 247/04* | (2006.01) |
| *C07C 17/16* | (2006.01) |
| *C07C 231/02* | (2006.01) |

(52) U.S. Cl.
CPC ............. *C07C 231/12* (2013.01); *C07C 17/16* (2013.01); *C07C 41/01* (2013.01); *C07C 41/18* (2013.01); *C07C 231/02* (2013.01); *C07C 237/06* (2013.01); *C07C 247/04* (2013.01); *C07C 303/40* (2013.01)

(58) Field of Classification Search
CPC . C07C 231/12; C07C 231/02; C07C 237/06; C07C 41/01; C07C 41/18; C07C 303/40; C07C 247/04; C07C 17/16
See application file for complete search history.

(56) References Cited

U.S. PATENT DOCUMENTS

| | | | |
|---|---|---|---|
| 2009/0149544 A1 | 6/2009 | Liu | |
| 2013/0204042 A1* | 8/2013 | Sriram | ................. C07C 227/16 564/158 |

FOREIGN PATENT DOCUMENTS

| | | |
|---|---|---|
| EP | 2 474 521 A1 | 7/2012 |
| WO | WO 98/03472 A1 | 1/1998 |
| WO | WO 2011/047767 * | 4/2011 |

OTHER PUBLICATIONS

Muthukrishnan and Mujahid, "A New Enantioselective Synthesis of the Anti-Parkinson Agent Safinamide," *Synthesis* (2014), 46:1751-1756, Georg Thieme Verlag, Stuttgart, New York.

* cited by examiner

*Primary Examiner* — Shailendra Kumar
(74) *Attorney, Agent, or Firm* — DLA Piper LLP (US)

(57) ABSTRACT

The present invention relates to an improved process for synthesis of anti-Parkinson compound of formula (I) from commercially available (R)-benzyl glycidyl ether, wherein the compound obtained has enantiopurity greater than >98%. Formula (I) wherein $R_1$ and $R_2$ are each independently selected from hydrogen or halogen.

Formula I

11 Claims, 4 Drawing Sheets

SYNTHESIS OF ANTI-PARKINSON AGENT

CROSS-REFERENCE TO RELATED APPLICATIONS

This application is a 35 USC §371 National Stage application of International Application No. PCT/IN2014/000294 filed May 2, 2014, now pending; which claims the benefit under 35 USC §119(a) to India Application Serial No. 1307/DEL/2013 filed May 3, 2013, now expired. The disclosure of each of the prior applications is considered part of and is incorporated by reference in the disclosure of this application.

FIELD OF THE INVENTION

The present invention relates to an improved process for synthesis of an anti-Parkinson compound of formula I from commercially available (R)-benzyl glycidyl ether. The compound produced by the process have high enantiopurity of greater than 98% (>98% ee).

BACKGROUND OF THE INVENTION

Figure 1:
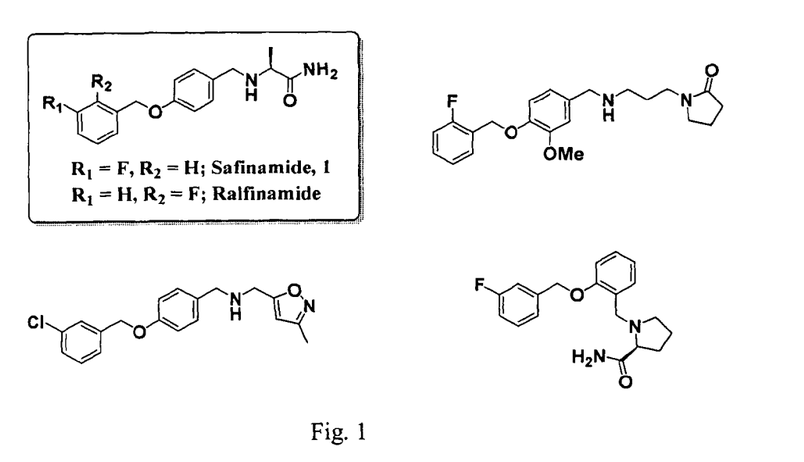
FIG. 1 provides few examples of pharmaceutically important benzyloxy-benzylamine derivatives.

Parkinson's disease (PD) is a progressive neurodegenerative disease characterized by bradykinesia, rigidity, resting tremor, and ataxia. These symptoms are caused by decreased dopamine release in the striatum. Clinically, PD is defined by presence of Lewy bodies, intracellular neuronal inclusions in the substantia nigra and at other sites in the brain. Estimated prevalence of this disease is 100 to 200 per 100,000 population including males and females across the entire age group. Current treatment for PD comprises dopaminergic medications that include levodopa, dopamine agonists (DAs), monoamine oxidase-B (MAO-B) inhibitors. FIG. 1 provides few examples of pharmaceutically important benzyloxy-benzylamine derivatives. Many of these benzyloxy-benzylamines with various amine functions were studied and has been patented as sodium channel blockers. Among them, safinamide ((S)-$N^2$-{4-[3-fluorobenzyl)oxy]benzyl}-alaninamide methanesulfonate) is a noted example which is under phase III clinical trials for treatment of Parkinson's disease. Its mechanism of action is manifold which comprise MAO-B and dopamine uptake inhibition. Further, safinamide is believed to block voltage-dependent sodium channels, modulates calcium channels and reduction of glutamate release in the central nervous system.

WO1998003472 discloses serinamide, glycinamide, alaninamide and phenylalaninamide derivatives of a compound (I). These compounds (I) are useful for the treatment of neurological diseases.

EP2474521 discloses high purity degree (S)-2-[4-(3-fluorobenzyloxy)-benzylamino]propanamide (safinamide) or (S)-2-[4-(2-fluorobenzyloxy)-benzylamino]propanamide (ralfinamide) or a salt thereof with a pharmaceutically acceptable acid with a content of the respective impurity (S)-2-[3-(3-fluorobenzyl)-4-(3-fluorobenzyloxy)-benzylamino]propanamide or (S)-2-[3-(2-fluorobenzyl)-4-(2-fluorobenzyloxy)-benzylamino]propanamide.

US2009149544 relates to novel alpha-aminoamide derivatives, their pharmaceutically acceptable salts, solvates, and hydrates thereof. The application also provides compositions comprising a compound and the use of such compositions in methods of treating diseases and conditions that are beneficially treated by administering an inhibitor of monoamine oxidase type B (MAO-B) and/or a sodium (Na.sup.+) channel blocker, and/or a calcium (Ca.sup.2+) channel modulator.

The strategy employed in the art to prepare benzyloxy-benzylamine derivatives including safinamide or its analogue ralfinamide is chiral pool approach starting from L-alaninamide and reductively aminating with 4-(3-fluorobenzyloxy)benzaldehyde. Although this method is very simple and straightforward, it suffers from several serious drawbacks, such as need to use toxic reagents such as sodium cyanoborohydride and further formation of toxic by-products such as hydrogen cyanide and sodium cyanide and other toxic impurities in large-scale production Importantly, the possibility of generating a range of safinamide analogues by means of the chiral-pool approach is limited in terms of the structure and stereochemistry of the products because of inadequacies in the availability of D-alaninamide and its analogues Hence, the developments of newer methods for the preparation of compounds of formula (I) comprising safinamide and related analogues are highly desirable.

OBJECTIVE OF THE INVENTION

The main object of the present invention is to provide an improved and efficient process for synthesis of an anti-Parkinson compound of formula (I) using commercially available substrate with enantiopurity greater than 98%.

Another object of the present invention is to provide an improved and efficient process for synthesis of safinamide.

Yet another object of the present invention is to provide an improved and efficient process for synthesis of ralfinamide.

SUMMARY OF THE INVENTION

The present invention relates to an efficient a process for preparation of an enantiomer of compound of formula I Formula I wherein $R_1$ and $R_2$ are each independently selected from hydrogen or halogen, said process comprising;
(a) regio selective reducing an epoxide (R)-compound 2 in presence of a reducing agent to obtain a secondary alcohol (R)-compound 3;
(b) mesylating the secondary alcohol (R)-compound 3 of step (a) followed by reacting with $NaN_3$ to obtain an azido derivative (S)-compound 4;
(c) hydrogenating/hydrogenolysis, of the azido derivative (S)-compound 4 obtained in step (b) with $Pd(OH)_2$ catalyst followed by N-nosylation using nosyl chloride under basic conditions to obtain amino alcohol (S)-compound 5;
(d) condensing amino alcohol (S)-compound 5 and alkyl iodide compound 9 in presence of a base and a solvent to obtain a coupled product (S)-compound 10;
(e) oxidizing the coupled product (S)-compound 10 using TEMPO or bleach conditions to obtain an acid (S)-compound 11;

(f) reacting the acid (S)-compound 11 of step (e) with ethylchlorofomate in presence of Et₃N and a solvent followed by reaction with aqueous NH₃ to obtain an amide (S)-compound 12; and (g) treating said amide (S)-compound 12 with thiophenol in presence of a base and a solvent to obtain the enantiomer of compound of formula I.

The present invention further relates to an enantiomer of compound of formula I prepared by the process for use in treatment of Parkinson's disease.

DETAILED DESCRIPTION OF THE INVENTION

The present invention discloses a process for preparation of an enantiomer of compound of formula I Formula I wherein $R_1$ and $R_2$ are each independently selected from hydrogen or halogen, said process comprising;

a. regio selective reducing an epoxide (R)-compound 2 in presence of a reducing agent to obtain a secondary alcohol (R)-compound 3;

(R)-compound 2

(R)-compound 3 b. mesylating the secondary alcohol (R)-compound 3 of step (a) followed by reacting with NaN₃ to obtain an azido derivative (S)-compound 4;

(S)-compound 4 c. hydrogenating/hydrogenolysis of the azido derivative (S)-compound 4 obtained in step (b) with Pd(OH)₂ catalyst followed by N-nosylation using nosyl chloride under basic conditions to obtain amino alcohol (5)-compound 5;

(S)-compound 5 d. condensing amino alcohol (S)-compound 5 and alkyl iodide compound 9 in presence of a base and a solvent to obtain a coupled product (S)-compound 10;

Compound 9 wherein $R_1$ and $R_2$ are each independently selected from hydrogen or halogen;

(S)-compound 10 wherein $R_1$ and $R_2$ are each independently selected from hydrogen or halogen;

e. oxidizing the coupled product (S)-compound 10 using TEMPO/bleach conditions to obtain an acid (S)-compound 11;

(S)-compound 11 wherein $R_1$ and $R_2$ are each independently selected from hydrogen or halogen f. reacting the acid (S)-compound 11 of step (e) with ethylchlorofomate in presence of Et₃N and a solvent followed by reaction with aqueous NH₃ to obtain an amide (S)-compound 12;

(S)-compound 12 wherein $R_1$ and $R_2$ are each independently selected from hydrogen or halogen g. treating said amide (S)-compound 12 with thiophenol in presence of a base and a solvent to obtain the enantiomer of compound of formula I.

In an embodiment of the present invention, there is provided a process for preparation of an enantiomer of compound of formula I, wherein the enantiomer of compound of Formula I is salified with methane sulphonic acid to obtain a salt of said compound.

In yet another embodiment of the present invention there is provided a process for preparation of an enantiomer of compound of formula I, wherein the reducing agent is a hydride reducing agent selected from the group consisting of LiAlH$_4$, NaBH$_4$, Zn(BH$_4$)$_2$ and borane.

In still another embodiment of the present invention, there is provided a process for preparation of an enantiomer of compound of formula I, wherein the base used in step (d) and step (g) is an organic base selected from the group consisting of ethylamine, diethylamine and pyridine; or an inorganic base selected from the group consisting of alkali or alkaline metal carbonates or bicarbonates.

In another embodiment of the present invention, there is provided a process for preparation of an enantiomer of compound of formula I, wherein the base used in step (d) and step (g) is an organic base selected from the group consisting of ethylamine, diethylamine and pyridine.

In yet another embodiment of the present invention there is provided a process for preparation of an enantiomer of compound of formula I, wherein the base used in step (d) and step (g) is an inorganic base selected from the group consisting of alkali or alkaline metal carbonates or bicarbonates.

In still another embodiment of the present invention there is provided a process for preparation of an enantiomer of compound of formula I, wherein the solvent used in step (d), step (f) and step (g) is a polar aprotic solvent selected from the group consisting of acetonitrile, THF, DCM, ethyl acetate and DMF.

In another embodiment of the present invention, there is provided a process for preparation of alkyl iodide (compound 9), said process comprising;
a. iodinating compound 6 using triphenylphosphine and iodoimidazole generated in situ by iodine and imidazole to obtain a compound 7;

Compound 6 wherein R$_1$ and R$_2$ are each independently selected from hydrogen or halogen Compound 7 wherein R$_1$ and R$_2$ are each independently selected from hydrogen or halogen;

b. reacting compound 7 with 4-(hydroxymethyl) phenol under basic condition to obtain an O-alkylated product 8; and Compound 8 wherein R$_1$ and R$_2$ are each independently selected from hydrogen or halogen;

c. iodinating compound 8 to obtain the alkyl iodide compound 9

Compound 9 wherein R1 and R2 are each independently selected from hydrogen or halogen.

In an embodiment of the present invention there is provided a process for preparation of an enantiomer of compound of formula I, wherein the compound of formula (I) is safinamide.

Safinamid

In another embodiment of the present invention there is provided a process for preparation of an enantiomer of compound of formula I, wherein the compound of formula (I) is ralfinamide.

Ralfinamide

In yet another embodiment of the present invention there is provided a process for preparation of an enantiomer of compound of formula I, wherein said compound obtained has an enantiopurity greater than 98%.

In still another embodiment of the present invention there is provided a process for preparation of an enantiomer of compound of formula I, wherein the yield of the enantiomer of compound of formula I is in the range of 85% to 90%.

An embodiment of the present invention provides an enantiomer of compound of formula I prepared by the process of the present invention for use in treatment of Parkinson's disease.

Figure 2:
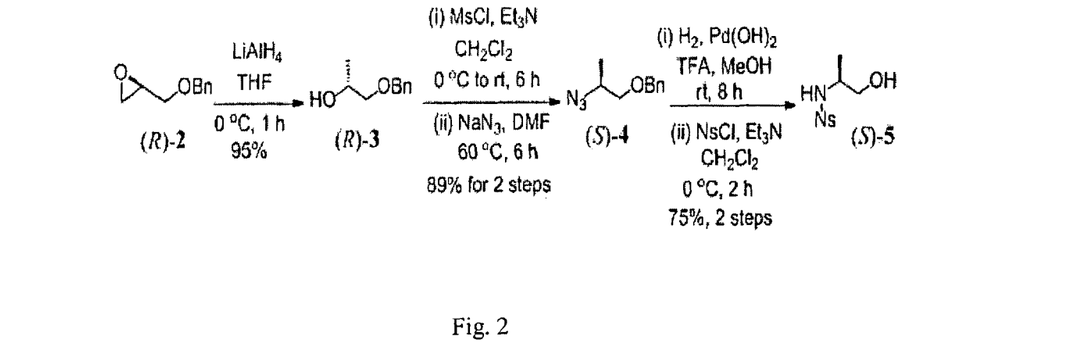
FIG. 2 provides the scheme for the synthesis of (S)-compound 5 from (R)-compound 2.
Figure 3:
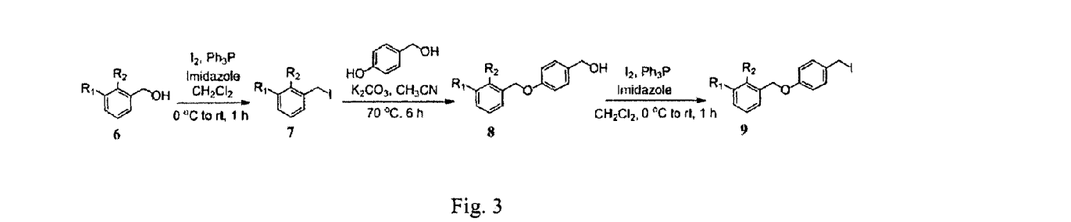
FIG. 3 provides the scheme for the synthesis of compound 9 from compound 6.
Figure 4:
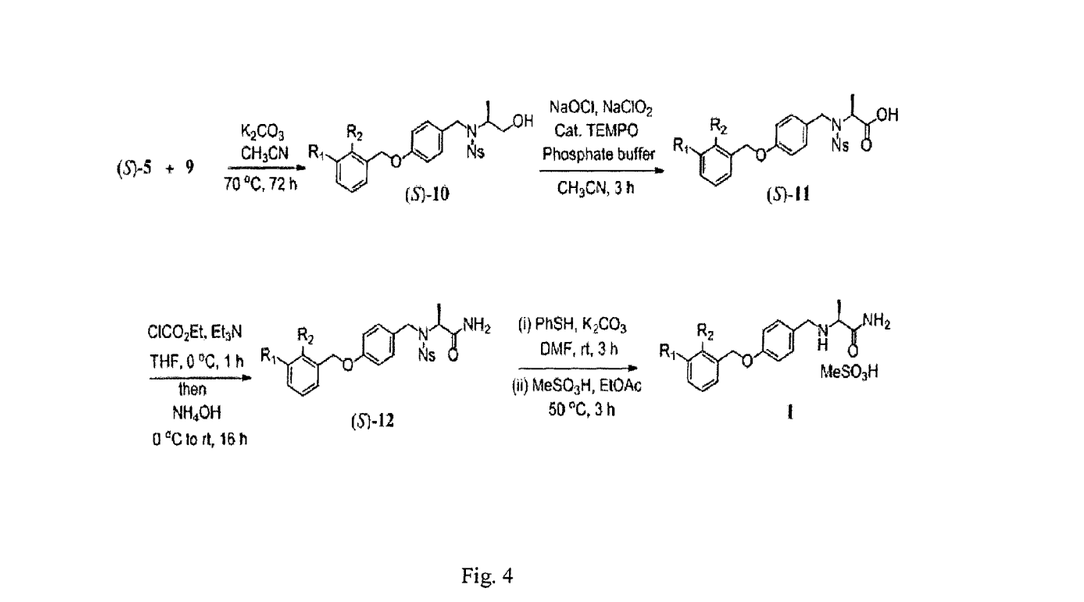
FIG. 4 provides the scheme for the synthesis of compound of formula I from (S)-compound 5 and compound 9.

FIG. 2 provides the scheme for synthesis of (S)-compound 5 from (R)-compound 2. As observed from the scheme, the amino alcohol (S)-compound 5 is prepared from commercially available (R)-benyl glycidyl ether. FIG. 3 provides the scheme for the synthesis of compound 9 from compound 6. As observed from the scheme, the iodo fragment compound 9 is prepared from commercially available suitably substituted fluoro benyl alcohol (compound 6). FIG. 4 provides the scheme for the synthesis of compound of formula I from (S)-compound 5 and compound 9.

Figure 5:
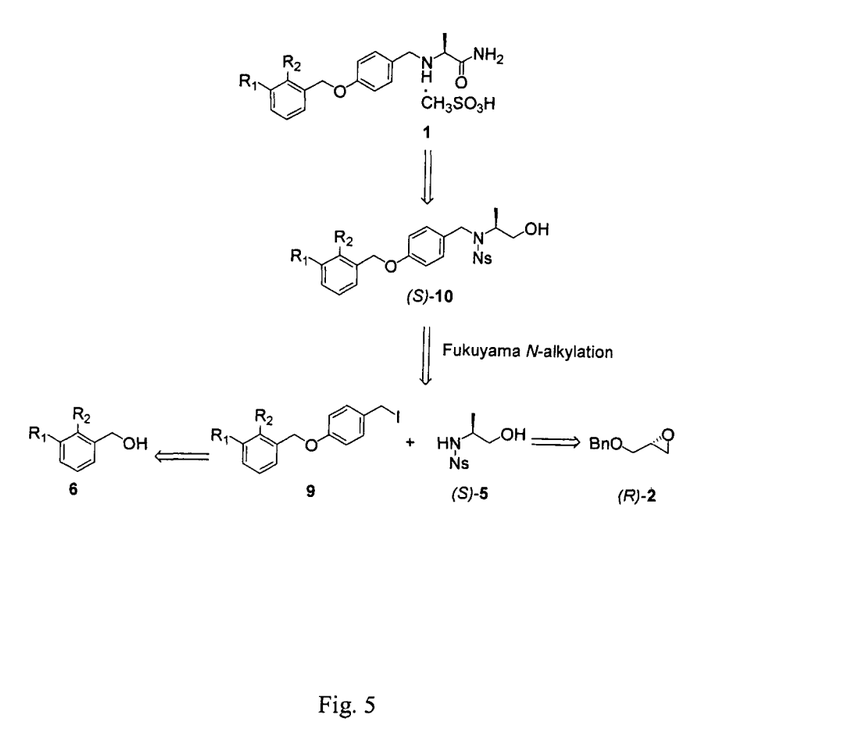
FIG. 5 provides the retrosynthetic analysis of sulfonamide.
Figure 6A:
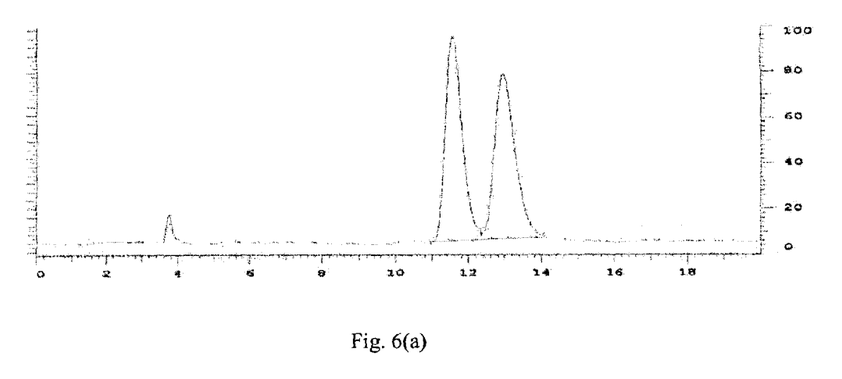
FIGS. 6(a) and 6(b) depicts Racemic and Chiral (ee>98%) HPLC chromatogram of Safinamide. Conditions: Column—Chiralcel OD-RH (250×4.6 mm), M.P: Methanol/Acetonitrile/Buffer-TEAP, pH 3 (20:10:70); Wavelength-224 nm.
Figure 6B:
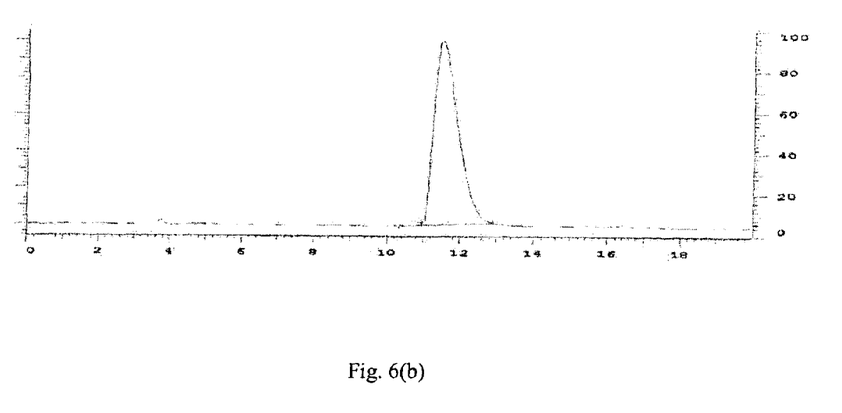

The present invention provides Safinamide with >98% ee. The structure of safinamide was confirmed by its IR, $^1$H NMR, $^{13}$C NMR and mass spectroscopic analysis. The enantiomeric purity of safinamide was determined by chiral HPLC analysis. FIG. 5 provides the retrosynthetic analysis of sulfonamide. FIGS. 6(a) and 6(b) depicts Racemic and Chiral (ee>98%) HPLC chromatogram of Safinamide. Conditions: Column—Chiralcel OD-RH (250×4.6 mm), M.P: Methanol/Acetonitrile/Buffer-TEAP, pH 3 (20:10:70); Wavelength-224 nm.

EXAMPLES

The invention will now be illustrated with help of examples. The aforementioned embodiments and below mentioned examples are for illustrative purpose and are not meant to limit the scope of the invention. Various modifications of aforementioned embodiments and below mentioned examples are readily apparent to a person skilled in the art.

Example 1

General

Solvents were purified and dried by standard procedures prior to use. $^1$H NMR and $^{13}$C NMR spectra were recorded on a Bruker AC-200 NMR spectrometer. Spectra were obtained in $CDCl_3$. The reactions were monitored by using TLC plates Merck Silica Gel 60 F254 and visualization with UV light (254 and 365 nm), $KMnO_4$ and anisaldehyde in ethanol as development reagents. Optical rotations were measured with a JASCO P 1020 digital polarimeter. Enantiomeric excesses were determined by chiral HPLC, performed on 'SHIMADZU SCL-10A unit' system controller and UV monitor as detector.

Example 2

Synthesis of (R)-1-(benzyloxy)propan-2-ol [(R)-Compound 3]

To a solution of (R)-benzyl glycidyl ether [(R)-compound 2] (4 g, 24.4 mmol) in dry THF (10 mL) at 0° C., a pre-cooled solution of lithium aluminium hydride (1.4 g, 36.6 mmol) in anhydrous THF (10 mL) was added slowly with stirring under nitrogen. After 60 min, the reaction mixture was quenched with 1 ml of water and 1 ml of 15% NaOH solution and the content was stirred for 15 min. The inorganic precipitate was filtered, washed with ethyl acetate and the solvent evaporated under reduced pressure. The residue was purified by a short filtration column to afford (R)-compound 3 as a colorless oil (3.8 g, 95%); $[\alpha]^{22}_D=-14.5$ (c 2, $CHCl_3$); IR ($CHCl_3$): $\nu_{max}$ 3418, 3087, 3063, 3030, 2963, 2924, 1952, 1873, 1600, 1495, 1454, 1363, 1244, 1099, 1028, 918, 808, 698 $cm^{-1}$; $^1$H NMR (200 MHz, $CDCl_3$): $\delta_H$ 1.13 (d, J=6.3 Hz, 3H), 2.5 (bs, 1H), 3.23-3.32 (dd, J=9.8, 1.3 Hz, 1H), 3.43-3.49 (dd, J=9.45, 3.2 Hz, 1H), 3.91-4.03 (m, 1H), 4.55 (s, 2H), 7.25-7.37 (m, 5H); $^{13}$C NMR (50 MHz, $CDCl_3$): $\delta_C$ 137.8 (C), 128.3 (CH, 2 carbons), 127.7 (CH, 3 carbons), 75.7 ($CH_2$), 73.2 ($CH_2$), 66.4 (CH), 18.6 ($CH_3$); MS: m/z 189 $[M+Na]^+$.

Example 3

Synthesis of (S)-((2-azidopropoxy)methyl)benzene [(S)-Compound 4]

To a stirred solution of secondary alcohol (R)-compound 3 (3 g, 18.1 mmol) in dry dichloromethane (25 mL), $Et_3N$ (3.1 mL, 21.7 mmol) at 0° C. was added, followed by drop wise addition of mesyl chloride (1.8 mL, 21.7 mmol). The reaction mixture was stirred at 0° C. for 2 hours, subsequently at room temperature for 3 hours under a nitrogen atmosphere. After completion of the reaction (indicated by TLC), the reaction mixture was diluted with dichloromethane and washed with a saturated solution of sodium bicarbonate (30 mL) and water (2×10 mL). The organic layer was separated, dried over anhydrous $Na_2SO_4$, filtered, and concentrated under reduced pressure to give the O-mesyl compound (4.3 g; crude).

To a solution of the crude O-mesyl compound (4 g, 16.37 mmol) in dry DMF (10 mL), sodium azide (1.6 g, 24.55 mmol) was added and the reaction mixture was heated at 60° C. for 6 hours under nitrogen atmosphere. After completion of the reaction (indicated by TLC), water (10 mL) was added to the reaction mixture, then extracted with ethyl acetate (2×15 mL). The combined organic layers were washed with brine solution, dried over anhydrous $Na_2SO_4$, filtered, and concentrated under reduced pressure. Purification of the crude residue was done by column chromatography (silica gel, petroleum ether/EtOAc, 95:5) to yield (S)-compound 4 as a colorless oil. (2.8 g; 89%); $[\alpha]^{22}_D=+6.1$ (c 1.3, $CHCl_3$); IR ($CHCl_3$): $\nu_{max}$ 3394, 3032, 2977, 2864, 2500, 2104, 1724, 1641, 1496, 1454, 1363, 1269, 1101, 913, 698 $cm^{-1}$; $^1$H NMR (200 MHz, $CDCl_3$): $\delta_H$ 1.20 (d, J=6.7 Hz, 3H), 3.39-3.54 (m, 2H), 3.61-3.77 (m, 1H), 4.57 (s, 2H), 7.25-7.39 (m, 5H); $^{13}$C NMR (50 MHz, $CDCl_3$): $\delta_C$ 137.8 (C), 128.4 (CH, 2 carbons), 127.7 (CH), 127.5 (CH, 2 carbons), 73.7 ($CH_2$), 73.2 ($CH_2$), 56.9 (CH), 16.1 ($CH_3$); MS: m/z 214 $[M+Na]^+$.

Example 4

Synthesis of (S)-N-(1-hydroxypropan-2-yl)-2-nitrobenzenesulfonamide [(S)-Compound 5]

To a solution of (S)-compound 4 (2.5 g, 13.1 mmol) in methanol (15 mL), trifluoroacetic acid (2 mL) and palladium hydroxide on activated carbon (0.05 g, 10-20 wt %) were added and the reaction mixture was stirred under hydrogen (60 psi) for 8 hours. After completion of the reaction (indicated by TLC), the catalyst was filtered over a plug of celite and the solvent was evaporated under reduced pressure to half of its volume which was basified with 2.5 M methanolic NaOH. Evaporation of the remaining solvent under reduced pressure was done followed by filtration of the residue through a short bed of basic alumina (eluent; MeOH) to obtain the amino alcohol as a pale brown oil (0.94 g, crude) which was subjected to the next reaction without further purification.

To a solution of amino alcohol (0.9 g, 11.98 mmol) in dry dichloromethane (5 mL), 2-nitrobenzenesulfonylchloride (3.2 g, 14.37 mmol) in dichloromethane (8 mL) and triethylamine (2.6 mL, 17.97 mmol) at 0° C. were slowly added under nitrogen atmosphere. The solution was stirred for 2 hours. After completion of the reaction (indicated by TLC), water (10 mL) was added to the reaction mixture, then extracted with dichloromethane (2×15 mL). The combined organic layers were washed with brine solution, dried over anhydrous $Na_2SO_4$, filtered, and concentrated under reduced pressure. Purification of the crude residue was done by column chromatography (silica gel, petroleum ether/EtOAc, 60:40) to yield (S)-compound 5 as a pale yellow oil (2.33 g, 75%); $[\alpha]^{22}_D$=+80.2 (c 2.1, $CHCl_3$); IR ($CHCl_3$): $\nu_{max}$ 3546, 3367, 3022, 2883, 2401, 1594, 1542, 1412, 1362, 1216, 1170, 1125, 1059, 971, 854, 668 $cm^{-1}$; $^1$H NMR (200 MHz, $CDCl_3$): $\delta_H$ 1.13 (d, J=6.5 Hz, 3H), 2.16 (bs, 1H), 3.45-3.70 (m, 3H), 5.61 (d, J=6.6 Hz, 1H), 7.73-7.80 (m, 2H), 7.86-7.91 (m, 1H), 8.13-8.22 (m, 1H); $^{13}$C NMR (50 MHz, $CDCl_3$): $\delta_C$ 147.8 (C), 134.4 (C), 133.7 (CH), 133.0 (CH), 130.9 (CH), 125.5 (CH), 66.2 ($CH_2$), 52.5 (CH), 17.8 ($CH_3$); MS: m/z 283 [M+Na]$^+$.

Example 5

Synthesis of 1-fluoro-3-(iodomethyl)benzene (Compound 7)

To a stirred solution of triphenyl phosphine (4.15 g, 15.85 mmol), imidazole (1.1 g, 15.85 mmol) in dry dichloromethane (20 mL), iodine (4.8 g, 19.02 mmol) at 0° C. was added and the solution was stirred for 5 min. To this, 3-fluoro benzyl alcohol (compound 6) (2 g, 15.85 mmol) dissolved in dichloromethane (5 mL) was added drop wise over 10 min and the stirring was continued for 1 hour with exclusion of light. After completion of the reaction (indicated by TLC), the reaction mixture was quenched by addition of an aqueous $Na_2S_2O_3$ solution (15 mL), then extracted with dichloromethane (2×20 mL). The combined organic layers were washed with brine solution, dried over anhydrous $Na_2SO_4$, filtered, and concentrated under reduced pressure. Purification of the crude residue was done by column chromatography (silica gel, petroleum ether/EtOAc, 95:5) to yield compound 7 as a colorless oil (3.5 g, 95%); (IR ($CHCl_3$): $\nu_{max}$ 3460, 3060, 2965, 1695, 1613, 1593, 1482, 1446, 1259, 1156, 1068, 944, 871, 782, 736, 686 $cm^{-1}$; $^1$H NMR (200 MHz, $CDCl_3$): $\delta_H$ 4.42 (s, 2H), 6.89-6.99 (m, 1H), 7.05-7.17 (m, 2H), 7.21-7.29 (m, 1H); $^{13}$C NMR (50 MHz, $CDCl_3$): $\delta_C$ 165.0 (C), 141.6 (C), 130.2 (CH), 124.4 (CH), 115.9 (CH), 114.7 (CH), 3.9 ($CH_2$).

Example 6

Synthesis of (4-((3-flurobenzyl)oxy)phenyl)methanol (Compound 8)

To a stirred solution of 4-(hydroxymethyl)phenol (1.57 g, 12.7 mmol) and $K_2CO_3$ (8.8 g, 63.55 mmol) in dry acetonitrile (25 mL), compound 7 (3 g, 12.7 mmol) in acetonitrile was slowly added and the reaction mixture was heated at 70° C. for 6 hours. After completion of the reaction (indicated by TLC), water (20 mL) was added to the reaction mixture, then extracted with ethylacetate (3×20 mL). The combined organic layers were washed with brine solution, dried over anhydrous $Na_2SO_4$, filtered, and concentrated under reduced pressure. Purification of the crude residue was done by column chromatography (silica gel, petroleum ether/EtOAc, 70:30) to yield compound 8 as a colorless solid (2.7 g, 91%); mp 63-65° C.; IR ($CHCl_3$): $\nu_{max}$ 3422, 3017, 1612, 1512, 1489, 1381, 1216, 1174, 1020, 829, 668 $cm^{-1}$; $^1$H NMR (200 MHz, $CDCl_3$): $\delta_H$ 4.61 (s, 2H), 5.06 (s, 2H), 6.91-6.98 (m, 2H), 7.00-7.06 (m, 1H), 7.12-7.20 (m, 2H), 7.25-7.37 (m, 3H); $^{13}$C NMR (50 MHz, $CDCl_3$): $\delta_C$ 165.4 (C), 160.5 (C), 158.0 (C), 139.6 (C), 133.5 (CH), 130.2 (CH), 128.7 (CH, 2 carbons), 122.7 (CH), 114.8 (CH, 2 carbons), 113.9 (CH), 69.1 ($CH_2$), 64.9 ($CH_2$); MS: m/z 255 [M+Na]$^+$.

Example 7

Synthesis of 1-fluoro-3-((4-(iodomethyl)phenoxy)methyl)benzene (Compound 9)

To a stirred solution of triphenyl phosphine (2.82 g, 10.8 mmol), imidazole (0.73 g, 10.76 mmol) in dry dichloromethane (20 mL), iodine (3.27 g, 12.9 mmol) at 0° C. was added and the solution was stirred for 5 min. To this, compound 8 (2.5 g, 10.8 mmol) dissolved in dichloromethane (5 mL) was added drop wise over 10 min and the stirring was continued for 1 hour with exclusion of light. After completion of the reaction (indicated by TLC), the reaction mixture was quenched by addition of an aqueous $Na_2S_2O_3$ solution (15 mL), then extracted with dichloromethane (2×20 mL). The combined organic layers were washed with brine solution, dried over anhydrous $Na_2SO_4$, filtered, and concentrated under reduced pressure. Purification of the crude residue was done by column chromatography (silica gel, petroleum ether/EtOAc, 95:5) to yield compound 9 as a colorless oil (3.4 g, 93%); IR ($CHCl_3$): $\nu_{max}$ 3503, 3033, 2925, 2089, 1607, 1509, 1488, 1381, 1301, 1250, 1155, 1079, 944, 869, 776, 684 $cm^{-1}$; $^1$H NMR (200 MHz, $CDCl_3$): $\delta_H$ 4.47 (s, 2H), 5.04 (s, 2H), 6.85-6.91 (m, 2H), 6.96-7.02 (m, 1H), 7.05-7.12 (m, 1H), 7.16-7.20 (m, 1H), 7.29-7.40 (m, 3H). $^{13}$C NMR (50 MHz, $CDCl_3$): $\delta_C$ 165.4 (C), 160.5 (C), 158.1 (C), 131.9 (C), 130.2 (CH), 130.1 (CH, 2 carbons), 122.7 (CH), 115.1 (CH, 2 carbons), 114.7 (CH), 113.9 (CH), 69.2 ($CH_2$), 6.33 ($CH_2$).

Example 8

Synthesis of (S)-N-(4-((3-flurobenzyl)oxy)benzyl)-N-(1-hydroxypropan-2-yl)-2-nitrobenzenesulfonamide [(S)-Compound 10]

To a stirred solution of (S)-compound 5 (1 g, 3.8 mmol) and $K_2CO_3$ (2.65 g, 19.2 mmol) in dry acetonitrile (25 mL), compound 9 (1.84 g, 5.4 mmol) in acetonitrile was slowly added and the reaction mixture was heated at 70° C. for 72 hours. After completion of the reaction (indicated by TLC), water (20 mL) was added to the reaction mixture, then extracted with ethylacetate (3×15 mL). The combined organic layers were washed with brine solution, dried over anhydrous $Na_2SO_4$, filtered, and concentrated under reduced pressure. Purification of the crude residue was done by column chromatography (silica gel, petroleum ether/EtOAc, 80:20) to yield (S)-compound 10 as a colorless oil (1.46 g, 80%); $[\alpha]^{22}_D$=+5.4 (c 1.5, $CHCl_3$); IR ($CHCl_3$): $\nu_{max}$ 3445, 3020, 2928, 2400, 1613, 1544, 1512, 1453, 1371, 1216, 1162, 1029, 852, 668 $cm^{-1}$; NMR (200 MHz, $CDCl_3$): $\delta_H$ 1.07 (d, J=6.9 Hz, 3H), 1.91 (t, J=5.2 Hz, 1H), 3.41-3.53 (m, 2H), 4.05-4.22 (m, 1H), 4.37-4.57 (m, 2H), 5.02 (m, 2H), 6.87 (d, J=8.53 Hz, 2H), 6.97-7.12 (m, 2H), 7.20 (d, J=7.2 Hz, 2H), 7.32 (d, J=8.7 Hz, 2H), 7.47-7.67 (m, 3H), 7.89 (d, J=8.09 Hz, 1H); $^{13}$C NMR (50 MHz, CDCl$_3$): $\delta_C$ 165.5 (C), 160.6 (C), 158.4 (C), 147.7 (C), 139.6 (C), 134.1 (C), 133.4 (CH), 131.6 (CH), 131.4 (CH), 1303 (CH), 129.7 (CH, 2 carbons), 124.1 (CH), 122.8 (CH), 115.1 (CH), 114.9 (CH, 2 carbons), 114.0 (CH), 69.2 (CH$_2$), 64.3 (CH$_2$), 56.2 (CH), 46.9 (CH$_2$), 15.4 (CH$_3$); MS: m/z 497 [M+Na]$^+$.

Example 9

Synthesis of (S)-2-(N-(4-((3-fluorobenzyl)oxy)benzyl)-2-nitrophenylsulfonamido) propanoic acid [(S)-Compound 11]

A mixture of (S)-compound 10 (1.25 g, 2.6 mmol), TEMPO (0.028 g, 0.18 mmol), acetonitrile (20 mL), and sodium phosphate buffer (16 mL, 0.67 M, pH 6.7) was heated to 35° C. Next, sodium chlorite (0.47 g dissolved in 2 mL water, 7.9 mmol) and diluted bleach (4-6%, 0.09 mL diluted in 1 mL water) were added simultaneously over 1 hour. The reaction mixture was stirred at 35° C. until the reaction was complete (3 hours, TLC), then cooled to room temperature. Water (30 mL) was added and the pH adjusted to 8 with 2 M NaOH. The reaction was quenched by pouring it into ice cold Na$_2$SO$_3$ solution maintained at <20° C. After stirring for 30 min at room temperature, ethyl acetate (20 mL) was added and the stirring was continued for an additional 15 min. The organic layer was separated and discarded. More ethyl acetate (20 mL) was added, and the aqueous layer was acidified with 1 M HCl to pH 3-4. The organic layer was separated, washed with water (2×15 mL), brine and concentrated under reduced pressure to afford the carboxylic acid (S)-compound 11 (1.1 g, 85%); $[\alpha]^{22}_D$=−20.4 (c 1.1, CHCl$_3$); IR (CHCl$_3$): $v_{max}$ 3398, 3095, 1718, 1612, 1591, 1543, 1512, 1489, 1457, 1371, 1303, 1251, 1163, 1059, 900, 852, 831, 778, 684 cm$^{-1}$; $^1$H NMR (200 MHz, CDCl$_3$): $\delta_H$ 1.44 (d, J=7.3 Hz, 3H), 4.23 (d, J=15.6 Hz, 1H), 4.64 (d, J=15.6 Hz, 1H), 4.82-4.90 (q, J=7.4 Hz, 1H), 4.92 (s, 2H), 6.68 (d, J=8.6 Hz, 2H), 6.89-7.01 (m, 2H), 7.07-7.13 (m, 3H), 7.18-7.33 (m, 2H), 7.43-7.55 (m, 3H), 8.81 (bs, 1H); $^{13}$C NMR (50 MHz, CDCl$_3$): $\delta_C$ 176.5 (CO), 165.0 (C), 158.0 (C), 147.4 (C), 139.4 (C), 134.1 (C), 133.2 (CH), 131.4 (CH), 130.3 (CH), 129.7 (CH, 2 carbons), 128.4 (C), 124.1 (CH), 122.6 (CH), 115.0 (CH), 114.6 (CH, 2 carbons), 114.3 (CH), 113.8 (CH) 69.1 (CH$_2$), 56.1 (CH), 49.0 (CH$_2$), 16.8 (CH$_3$); MS: m/z 511 [M+Na]$^+$.

Example 10

Synthesis of (S)-2-(N-(4-((3-fluorobenzyl)oxy)benzyl)-2-nitrophenylsulfonamido)propanamide [(S)-Compound 12]

To a solution of carboxylic acid (S)-compound 11 (1 g, 2.04 mmol) and triethyl amine (0.34 mL, 2.4 mmol) in dry THF (20 mL), ethyl chloroformate (0.21 mL, 2.2 mmol) at 0° C. was added under nitrogen atmosphere. After 1 hour, ammonium hydroxide (25% w/v aqueous solution, 1.4 mL, 10.2 mmol) was added and the resulting reaction mixture was stirred at room temperature for 16 hours. After completion of the reaction, potassium carbonate (0.29 g, 2.1 mmol) was added and the reaction mixture was filtered, and washed with ethylacetate. The solvent was removed under reduced pressure and the crude product was subjected to column chromatography (silica gel, petroleum ether/EtOAc, 50:50) to obtain sulfonamide (S)-compound 12 as a colorless oil (0.9 g, 91%); $[\alpha]^{22}_D$=−32.1 (c 1.2, CHCl$_3$); IR (CHCl$_3$): $v_{max}$ 3472, 1961, 1611, 1592, 1542, 1511, 1449, 1371, 1304, 1243, 1163, 1060, 1029, 895, 852, 684 cm$^{-1}$; $^1$H NMR (200 MHz, CDCl$_3$): $\delta_H$ 1.43 (d, J=7.1 Hz, 3H), 4.44 (d, J=15.4 Hz, 1H), 4.59 (d, J=15.5 Hz, 1H), 4.60-4.71 (q, J=7.0 Hz, 1H), 5.01 (s, 2H), 5.50 (bs, 1H), 6.31 (bs, 1H), 6.78 (d, J=8.71 Hz, 2H), 6.98-7.11 (m, 2H), 7.15-7.22 (m, 3H), 7.31-7.45 (m, 2H), 7.59-7.64 (m, 3H); $^{13}$C NMR (50 MHz, CDCl$_3$): $\delta_C$ 172.3 (CO), 165.5 (C), 158.2 (C), 147.5 (C), 139.6 (C), 139.4 (C), 133.6 (CH), 131.7 (CH), 130.5 (CH, 2 carbons), 130.3 (CH), 128.1 (C), 124.2 (CH), 122.7 (CH), 115.1 (CH), 114.7 (CH, 2 carbons), 114.4 (CH), 113.9 (CH), 69.0 (CH$_2$), 55.7 (CH), 48.3 (CH$_2$), 14.9 (CH$_3$); MS: m/z 510 [M+Na]$^+$.

Example 11

Synthesis of (S)-2-((4-((3-fluorobenzyl)oxy)benzyl)amino)propanamide [(S)-Compound of Formula I]

To a solution of sulfonamide (S)-compound 12 (0.8 g, 1.64 mmol), potassium carbonate (0.56 g, 4.9 mmol) in dry DMF (10 mL), thiophenol (0.2 mL, 1.9 mmol) was added. The reaction mixture was vigorously stirred for 6 hours. After completion of the reaction (indicated by TLC), water (10 mL) was added to the reaction mixture, then extracted with ethylacetate (2×20 mL). The combined organic layers were washed with brine solution, dried over anhydrous Na$_2$SO$_4$, filtered, and concentrated under reduced pressure. Purification of the crude residue was done by column chromatography (silica gel, petroleum ether/EtOAc, 60:40) to yield (S)-compound of formula I as a colorless solid (0.43 g, 86%); mp 207-09° C.; $[\alpha]^{22}_D$=+3.89 (c 1.55, CHCl$_3$); IR (CHCl$_3$): $v_{max}$ 3341, 2970, 2927, 2853, 1648, 1592, 1512, 1489, 1445, 1406, 1384, 1254, 1176, 1137, 1030, 953, 928, 829, 680 cm$^{-1}$; $^1$H NMR (200 MHz, CDCl$_3$): $\delta_H$ 1.34 (d, J=6.9 Hz, 3H), 2.49 (bs, 2H), 3.19-3.30 (q, J=6.8 Hz, 1H), 3.63-3.78 (dd, J=19.4, 3.9 Hz, 2H), 5.05 (s, 2H), 5.85 (bs, 1H), 6.95 (d, J=8.7 Hz, 2H), 7.00-7.06 (m, 1H), 7.13-7.24 (m, 4H), 7.29-7.40 (m, 1H). $^{13}$C NMR (50 MHz, CDCl$_3$): $\delta_C$ 178.3 (CO), 165.4 (C), 157.7 (C), 139.6 (C), 132.1 (C), 130.2 (CH), 129.3 (CH, 2 carbons), 122.7 (CH), 114.9 (CH, 2 carbons), 114.6 (CH), 113.9 (CH), 69.2 (CH$_2$), 57.5 (CH), 51.9 (CH$_2$), 19.6 (CH$_3$); MS: m/z 302 [M]$^+$, 325 [M+Na]$^+$.

Example 12

Synthesis of (S)-Safinamide Mesylate

To a stirred solution of (S)-compound of formula I (0.1 g, 0.33 mmol) in ethylacetate (3 mL) at 70° C., methanesulfonic acid (0.02 mL, 0.33 mmol) was added and the reaction mixture was stirred for 2 hours. Subsequently, the temperature was lowered to 35° C. and the stirring was continued for additional 1 hour. The solvent was evaporated under reduced pressure and the residue was filtered through a short bed of basic alumina [eluent: EtOAc/MeOH; (95:5)] to obtain safinamide mesylate as a white solid (0.11 g, 90%); mp 209-10° C. [lit.[7] mp 210]; $[\alpha]^{22}_D$=+9.6 (c 1.1, AcOH); {lit.[7] $[\alpha]^{22}_D$=+12.9 (c 1.1, AcOH)} ee>98% [The ee of safinamide mesylate was determined by chiral HPLC analysis; Chiralcel OD-RH (150×4.6 mm) column; eluent: Methanol/Acetonitrile/Buffer-TEAP, pH 3 (20:10:70); flow rate 0.5 mL/min (780 psi); detector: 224 nm] [(R)-isomer $t_R$=11.55 min, (S)-isomer $t_R$=12.94 min].

ADVANTAGES OF THE INVENTION

The process of the present invention does not use any toxic reagents. Further, the process does not lead to formation of any toxic byproducts.

The compound of formula I obtained by the process of the present invention has enantiopurity greater than 98% (ee>98%).

The compound of formula I produced by the process of the present invention is used for treatment of Parkinson's disease, restless legs syndrome and epilepsy.

We claim:

1. A process for preparation of an enantiomer of compound of formula I

Formula I wherein $R_1$ and $R_2$ are each independently selected from hydrogen or halogen, said process comprising;
a. regio selective reducing an epoxide (R)-compound 2 in presence of a reducing agent to obtain a secondary alcohol (R)-compound 3;

(R)-compound 2

(R)-compound 3 b. mesylating the secondary alcohol (R)-compound 3 of step (a) followed by reacting with NaN$_3$ to obtain an azido derivative (S)-compound 4;

(S)-compound 4 c. hydrogenating/hydrogenolysis of the azido derivative (S)-compound 4 obtained in step (b) with Pd(OH)$_2$ catalyst followed by N-nosylation using nosyl chloride under basic conditions to obtain amino alcohol (S)-compound 5;

(S)-compound 5 d. condensing amino alcohol (S)-compound 5 and alkyl iodide compound 9 in presence of a base and a solvent to obtain a coupled product (S)-compound 10;

Compound 9 wherein $R_1$ and $R_2$ are each independently selected from hydrogen or halogen;

(S)-compound 10 wherein $R_1$ and $R_2$ are each independently selected from hydrogen or halogen;
e. oxidizing the coupled product (S)-compound 10 using TEMPO or bleach conditions to obtain an acid (S)-compound 11;

(S)-compound 11 wherein $R_1$ and $R_2$ are each independently selected from hydrogen or halogen
f. reacting the acid (S)-compound 11 of step (e) with ethylchlorofomate in presence of Et$_3$N and a solvent followed by reaction with aqueous NH$_3$ to obtain an amide (S)-compound 12; and (S)-compound 12 wherein $R_1$ and $R_2$ are each independently selected from hydrogen or halogen
g. treating said amide (S)-compound 12 with thiophenol in presence of a base and a solvent to obtain the enantiomer of compound of formula I.

2. The process according to claim 1, wherein said process further comprises salification of compound of formula I with methane sulphonic acid to obtain a salt of compound of formula I.

3. The process according to claim 1, wherein the reducing agent is a hydride reducing agent selected from the group consisting of LiAlH$_4$, NaBH$_4$, Zn(BH$_4$)$_2$ and borane.

4. The process according to claim 1, wherein the base used in step (d) and step (g) is an organic base selected from the group consisting of ethylamine, diethylamine and pyridine; or an inorganic base selected from the group consisting of alkali or alkaline metal carbonates or bicarbonates.

5. The process according to claim 1, wherein the solvent is used in step (d), step (f) and step (g) is a polar aprotic solvent selected from the group consisting of acetonitrile, THF, DCM, ethyl acetate and DMF.

6. The process according to claim 1, wherein said alkyl iodide compound 9 used in step (d) is prepared by the process comprising;
   a. iodinating compound 6 using triphenylphosphine and iodoimidazole generated in situ by iodine and imidazole to obtain a compound 7;

Compound 6 wherein R$_1$ and R$_2$ are each independently selected from hydrogen or halogen

Compound 7 wherein R$_1$ and R$_2$ are each independently selected from hydrogen or halogen;
   b. reacting compound 7 with 4-(hydroxymethyl) phenol under basic condition to obtain an O-alkylated product 8; and Compound 8 wherein R$_1$ and R$_2$ are each independently selected from hydrogen or halogen; Iodinating compound 8 to obtain the alkyl iodide compound 9, Compound 9 wherein R1 and R2 are each independently selected from hydrogen or halogen.

7. The process according to claim 1, wherein the compound of formula (I) is safinamide, Salfinamide 8. The process according to claim 1, wherein the compound of formula (I) is ralfinamide, Ralfinamide 9. The process according to claim 1, wherein the compound obtained has an enantiopurity greater than 98%.

10. The process according to claim 1, wherein the yield of the enantiomer of compound of formula I is in the range of 85% to 90%.

11. A enantiomer of compound of formula I prepared by the process according to claim 1 for use in treatment of Parkinson's disease.

* * * * *